United States Patent [19]

Felder et al.

[11] Patent Number: 5,132,409
[45] Date of Patent: Jul. 21, 1992

[54] MACROCYCLIC CHELATING AGENTS AND CHELATES THEREOF

[75] Inventors: Ernst Felder, Rive S. Vitale, Switzerland; Carlo Musu, Milan, Italy; Luciano Fumagalli, Milan, Italy; Fulvio Uggeri, Milan, Italy

[73] Assignee: Bracco Industria Chimica S.P.A., Milan, Italy

[21] Appl. No.: 449,883

[22] PCT Filed: Dec. 16, 1988

[86] PCT No.: PCT/EP88/01166

§ 371 Date: Nov. 27, 1989

§ 102 (e) Date: Nov. 27, 1989

[87] PCT Pub. No.: WO89/05802

PCT Pub. Date: Jun. 29, 1989

Related U.S. Application Data

[63] Continuation-in-part of Ser. No. 2,115, Jan. 12, 1987, Pat. No. 4,916,246.

[30] Foreign Application Priority Data

Dec. 24, 1987 [IT] Italy ............... 232176 A/87

[51] Int. Cl.$^5$ ............... C07F 5/00; A61K 49/00
[52] U.S. Cl. ................... 534/10; 534/14; 534/15; 534/16; 540/450; 540/465; 540/452; 540/475; 424/1.1; 556/40; 556/44; 556/50; 556/56; 556/63; 556/77; 556/116; 556/125; 556/134; 556/136; 556/141; 556/148; 556/62; 556/115; 556/55; 556/133
[58] Field of Search ............... 534/16, 15, 10, 14; 540/450, 452, 465, 474; 424/1.1; 556/40, 44, 50, 55, 56, 62, 63, 77, 115, 116, 125, 134, 133, 136, 141, 148

[56] References Cited

U.S. PATENT DOCUMENTS 4,639,365  1/1987  Sherry .................... 424/9
4,885,363  12/1989  Tweedle et al. ............ 534/16 X
4,994,560  2/1991  Kruper, Jr. et al. ........ 534/10
5,006,643  4/1991  Fazio et al. .............. 534/10
5,049,667  9/1991  Schaefer et al. ........... 540/474

FOREIGN PATENT DOCUMENTS 0255471  7/1987  European Pat. Off. .
8901476  2/1989  PCT Int'l Appl. .

OTHER PUBLICATIONS

Desreux et al., "Highly Stable Lanthanide Macrocyclic Complexes", Nucl. Med. Biol. vol. 15, pp. 9-15, 1988.

Primary Examiner—Robert L. Stoll
Assistant Examiner—C. Sayala
Attorney, Agent, or Firm—Bucknam and Archer

[57] ABSTRACT

Macrocyclic derivatives of 1,4,7,10-tetraazacyclododecane of general formula (I) hereinbelow, wherein A is a group of formula (II) hereinbelow, in which R is H or alkyl or optionally substituted benzyl or a $H(OCH_2CH_2)_{1-4}$-, $Me(OCH_2CH_2)_{1-4}$-, or $Et(OCH_2CH_2)_{1-4}$-group, X or $O-R_1$, in which $R_1$ is H or alkyl, hydroxyalkyl, alkoxyalkyl, alkoxyhydroxyalkyl or a polyoxaalkyl group or X is $-NR_2R_3$, in which $R_2$ and $R_3$ are H or alkyl, hydroxyalkyl, alkoxyalkyl or alkoxyhydroxyalkyl, and $B_1$, $B_2$ and $B_3$ have the same meanings as A or are H or a group of formula (III) hereinbelow, in which $R_4$ is H or alkyl, Y is a $O-R_5$ group, wherein $R_5$ is H or alkyl, hydroxyalkyl, alkoxyalkyl, alkoxyhydroxyalkyl or a polyoxaalkyl group, or Y is a $-NR_6R_7$ group, wherein $R_6$ and $R_7$ are H or alkyl, hydroxyalkyl, alkoxyalkyl, or alkoxyhydroxyalkyl, said derivatives optionally being salified, and the complex salts thereof, are used as pharmaceuticals and/or diagnosic agents.

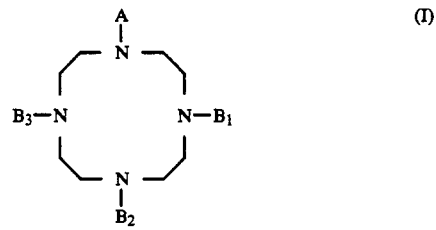

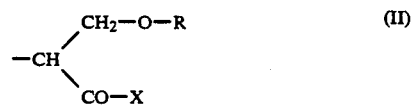

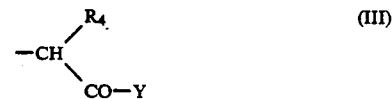

18 Claims, No Drawings

MACROCYCLIC CHELATING AGENTS AND CHELATES THEREOF

This application is the U.S. national phase of PCT Application No. PCT/EP88/01166 filed Dec. 16, 1988 which was based on Italian Patent Application No. 23217 A/87 which was filed on Dec. 24, 1987 and is also a Continuation-in-Part Application of U.S. Ser. No. 002,115 which was filed Jan. 12, 1987, now U.S. Pat. No. 4,916,246.

The present invention relates to novel macrocyclic chelating agents deriving from 1,4,7,10-tetraazacyclododecane of general formula I

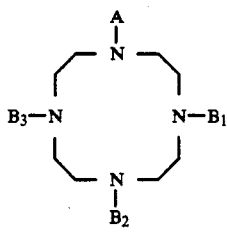

wherein
A is a group of formula

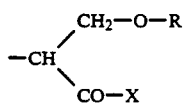

in which

R is H or a $C_1$-$C_5$ straight or branched alkyl group, or a benzyl group which can be mono- or polysubstituted on the aromatic ring by halogen, hydroxy, carboxy, carbamoyl, alkoxycarbonyl, sulphamoyl, lower alkyl, lower hydroxyalkyl, amino, acylamino, acyl, hydroxyacyl groups, or a group of formula $H(OCH_2CH_2)_{1-4}$-, $Me(OCH_2CH_2)_{1-4}$-, or $Et(OCH_2CH_2)_{1-4}$-, X is a $O-R_1$ group in which $R_1$ is H or a $C_1$-$C_5$ alkyl, hydroxyalkyl, alkoxyalkyl, alkoxyhydroxyalkyl group, or a polyoxaalkyl group having 1 to 15 oxygen atoms and 3 to 45 carbon atoms, or X is a $-NR_2R_3$ group in which $R_2$ and $R_3$, which can be the same or different, are $C_1$-$C_6$ alkyl, hydroxyalkyl, alkoxyalkyl or alkoxyhydroxyalkyl groups having up to 5 hydroxy groups and $B_1$, $B_2$ and $B_3$, which can be the same or different, have the same meaning as A or they are H or a group of formula

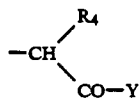

in which
$R_4$ is H or a $C_1$-$C_5$ straight or branched alkyl group,
Y is a $O-R_5$ group in which $R_5$ is H or a $C_1$-$C_5$ alkyl, hydroxyalkyl, alkoxyalkyl, alkoxyhydroxyalkyl group, or a polyoxaalkyl group having 1 to 15 oxygen atoms and 3 to 45 carbon atoms, or Y is a $-NR_6R_7$ group in which $R_6$ and $R_7$, which can be the same or different, are H or $C_1$-$C_6$ alkyl, hydroxyalkyl, alkoxyalkyl or alkoxyhydroxyalkyl groups having up to 5 hydroxy groups, said derivatives being, if necessary, salified with suitable organic or inorganic bases, and the complex salts of the abovesaid chelating agents with suitable metal ions in the acid, basic or neutral form or, if necessary, neutralized with inorganic or organic acid or base ions, and eventually chemically conjugated with macromolecules or incorporated in suitable carriers.

The present invention also relates to the preparation of compounds of general formula I and of the complex salts thereof, to their uses and, when indicated, to the pharmaceutical and diagnostic compositions thereof.

The chelating compounds of the present invention and the complex salts thereof can have a wide range of applications. No limiting examples of use of said chelating agents are the recovery, separation, selective extraction of metal ions even at very low concentrations, their therapeutical use as detoxifying agents in cases of inadvertent bodily incorporation of metals or radioisotopes, their use as ion carriers, or the other ones apparent to those skilled in the art. In such uses the chelating agents may be used directly or often they have been bonded covalently or non-covalently to macromolecules or insoluble surfaces or have been otherwise incorporated into structures that can carry them to specific sites.

In particular the complex salts of the chelating agents of formula I with the metal ions of the elements with atomic numbers of 20 to 31, 39, 42, 43, 44, 49 or 57 to 83 and, optionally, salified by physiologically biocompatible ions of organic or inorganic acids or organic or inorganic bases or aminoacids, are surprisingly suitable for use as contrast agents in medical diagnosis in nuclear medicine and in N.M.R., E.S.R., X-ray and/or ultrasonic diagnosis. Said derivatives, for the purpose of optimal diagnostic use, can also be bound or incorporated covalently or non-covalently into biomolecules, macromolecules or molecular aggregates characterized in that they can selectively concentrate in the organ or in the tissue under examination.

The imaging of internal structures of living subjects is becoming more and more relevant in medical diagnosis.

Among the most recent techniques, the use of radioisotopes as internal tracers in the organism should be mentioned. One of the biggest problems connected with the use of radioisotopes is their selectivity of distribution, while another important aspect is their excretion in an acceptable time.

Another imaging technique concerns with the use of ultrasounds to measure the difference in the reflections at the interfaces between tissues of different density. The administration of a suitable amount of a dense nonradioactive element or metal ion can give such a difference in reflectivity that can emphasize even small otherwise non detectable lesions.

A third diagnostic technique uses nuclear magnetic resonance to create internal images of the human body. In this field, the development of contrast agents is of particular importance for the following reasons:

a) to improve the specificity of the diagnosis,
b) to identify at an earlier stage small lesions,
c) to more precisely define the extension of a tumoral mass, d) to improve the signal to noise ratio and to shorten the time of acquisition of the images, allowing also better use of the instruments, e) to increase the contrast between those contiguous areas (for instance abdominal or pelvic) where it is particularly difficult to obtain well defined images, f) to obtain good informations on blood flow and on tissue perfusion.

As far as regards N.M.R. diagnosis, contrast media containing paramagnetic complex salts of lanthanides and transition metals have already been claimed for instance in patents EP 71564, U.S. Pat. Nos. 4,647,447, 4,687,658, 4,639,365, 4,678,667 and in patent applications DE 3401052, EP-A 135125, EP-A 130934, DE 3324236, EP-A 124766, EP-A 165728, WO 87/02893, EP-A 230893, EP-A 255471, EP-A 232751, EP-A 292689, EP-A 287465, WO 87/06229, WO 89/01475, WO 89/01476.

However all the till now developed contrast agents for N.M.R. present some problems as far as regards their capacity of influencing the relaxation time of the atomic nuclei involved, their often insufficient selectivity in bonding the metal ion, their stability, their selectivity for the organ under examination, or their biological tolerability. The tendency of many complexes to exchange the central metal ion with trace-metals essential to the organism or with ions, for example $Ca^{(2+)}$, which in vivo are present in relatively great amounts (see on the subject P.M. May "The present status of chelating agents in Medicine", page 233), further limits their possibilities of use. In fact, in case of insufficient stability of the complex, the organism may be deprived of trace-metals of vital importance and receive undesired and toxic heavy metals such as Gd, Eu or Dy. Although it is true that the toxicity of the complex is often, but not always, lower than the one of the free paramagnetic ion, it is also true that the complexation usually brings a decrease of the magnetic relaxation efficacy, responsible for some contrasting effects.

Several unsolved problems in connection with an optimal contrast agent therefore still remain, chiefly concerning: a strong effect on the relaxation time of the relevant nuclei, a high stability of the complex both in solution and in the organism, an adequate water solubility, a specificity of distribution in the various parts of the organism, a suitable rate of elimination from the involved organ and tissue.

One of the most studied paramagnetic metal ions is $Gd^{(3+)}$, in particular when complexed with the chelating agent diethylenetriamino-pentaacetic acid (DTPA) (Runge et al. (1983) Am. J. Radiol. V 141, p. 1209 and Weinman et al. (1984) Am. J. Radiol. V 142, p. 619). Said complex salified with D(−)N-methyl-glucamine is considered at the moment one of the most satisfying from the point of view of activity, toxicity and of its use in general.

However, in spite of these positive features, this compound cannot yet be considered fully respondent to the characteristics of an optimal contrast agent for various reasons, among which for instance the fact that Gd-DTPA/N-Methyl-D-glucamine is too quickly removed from the blood stream and from the lesions of the tissues under examination. This reduces the time available for obtaining images significant from diagnostic point of view. Moreover the diffusion of the contrast agent between the healthy part and the diseased one is often so fast that the contrast between the two regions can be too weak.

To overcome these difficulties, the problem has been approached in many ways among which the most interesting are:

a) Other chelating agents have been studied, in particular macrocyclic ones, of which the most effective proved to be 1,4,7,10-tetraazacyclododecane-N,N',N'',N'''-tetraacetic acid (DOTA). However its complexes continue to present problems analogous to the ones of DTPA.

b) Gadolinium and its chelating agents have been chemically conjugated to macromolecules such as, for instance, proteins (albumin, etc.), immunoglobulins, or to cellulose or other polymeric matrices. On the one hand this generally improved the relaxivity of Gd, but on the other hand it was necessarily accompanied by a sub-optimal dosage, because of limitations in solubility, toxicity and the substitution density of the macromolecules. Furthermore, when one of the ligand sites of the chelating agents is used to form the chemical bond with the macromolecule, there is also normally a reduction in the stability of the resulting complex.

The chelating agents of formula I have shown an excellent scavenging capacity for metal ions even in very diluted solutions. A significant example of said property is the capacity to capture the $Cu^{(2+)}$ ion from its aqueous solutions by 2-[1,4,7,10-tetraaza-4,7,10-tri(-carboxymethyl)-cyclododeca-ne-1-yl]-3-benzyloxypropionic acid, the method of synthesis of which is reported in examples 2 and 3.

With regards to their use in diagnosis, metal complexes with the chelating agents object of the present invention have proved surprisingly satisfying for instance with respect to the requirements for an N.M.R. contrast agent. Among the complexes particular importance is to be given to the complexes of $Gd^{(3+)}$, which distinguish themselves for excellent stability, relaxivity and selectivity for the organ or tissue under examination.

These compounds have a wide field of application, allowing administration by intravasal route (for example intravenous, intraarterial, intracoronaric, intraventricular, etc.), as well as intrathecal, intraperitoneal, intralymphatical, intracavital and intraparenchymal routes. Both the soluble and the poorly soluble compounds are suitable for oral or enteral administration, and therefore of particular usefulness for visualization of the gastrointestinal tract. For parenteral administration they are preferably formulated as a sterile aqueous suspension or solution, whose pH can range for instance from 6.0 to 8.5. Said sterile aqueous suspensions or solutions can be administered in concentrations varying from 0.002 to 1.0 molar.

Said formulations, can also be lyophilized and supplied as such, to be reconstituted at the moment of their use. For gastrointestinal use or for injection in body cavities said agents can be formulated as a suspension or a solution containing additives suitable for instance to increase viscosity.

For oral administration they can be formulated according to preparation methods commonly used in pharmaceutical technology, optionally also as a coated formulation so as to have additional protection against the acid pH of the stomach, preventing in that way the release of the chelated metal ions which takes place in particular at the pH values typical of gastric juices. Other excipients, such as sweetening or flavouring agents, can be added according to known pharmaceutical formulation techniques.

Suspensions or solutions of complex salts can also be formulated as aerosols to be used in aerosol-bronchography.

Some of the complex compounds of the invention have a surprising organ specificity, in that they particularly concentrate in the liver, in the spleen or, after intralymphatic, intraparenchymal, intramuscular or subcutaneous application, in the lymphatic vases and in the lymph nodes. The resulting contrast between the organ under examination and adjacent tissues permits improved imaging of said organ by N.M.R.

With regard to their use in diagnosis, metal complexes of the chelating agents object of the present invention can also be used as contrast agents in nuclear medicine and for electron spin resonance or echographic analyses.

In these cases however the metal central ions in the chelated complexes are, respectively, a radioisotope for example $^{51}Cr$, $^{68}Ga$, $^{111}In$, $^{99m}Tc$, $^{140}La$, $^{168}Yb$ or a non-radioisotope able to alter, owing to the density of its solutions, the speed of the ultrasonic waves transmitted and reflected.

In the compounds of general formula I, A is preferably a β-hydroxy-α-propionic, β-methoxy-α-propionic or β-benzyloxy-α-propionic group, optionally esterified or preferably substituted by an amide residue which can be free, mono-or bi-substituted by alkyl, hydroxyalkyl, alkoxyalkyl or alkoxyhydroxyalkyl groups.

R can preferably be H or a straight or branched alkyl group, such as a methyl, ethyl, propyl, isopropyl, butyl, isobutyl group or a benzyl or a substituted benzyl group as defined in formula I.

R can also be an acyl or hydroxyacyl group.

R can also be a polyoxaethylene group of formula $H(OHCH_2CH_2)_{2-4}$-, $Me(OCH_2CH_2)_{2-4}$-, o Et-$(OCH_2CH_2)_{2-4}$-.

X can be a hydroxy group or also a —O—$R_1$ group, wherein $R_1$ is as defined in formula I.

Non-limiting examples of $R_1$ are the following: methyl, ethyl, isopropyl, 2-hydroxyethyl, 2-hydroxypropyl, 1,3-dihydroxyisopropyl, polyoxaalkyl groups.

X can preferably be also an hydroxyalkylamino group of formula —$NR_2R_3$, in which $R_2$ and $R_3$ are as defined in formula I. Non-limiting examples of said groups are the following ones:
amino-, 2-hydroxyethylamino-, 2-hydroxypropylamino-, 2,3-dihydroxypropylamino-, 1,3-dihydroxyisopropylamino-, 1,3-dihydroxy-2-methyl-isopropylamino-, 2,3,4-trihydroxy-1-butylamino-, 1,3,4-trihydroxy-2-butylamino-, 1,3-dihydroxy-2-hydroxymethyl-isopropylamino-, N-methyl-N-2-hydroxyethylamino-, N-methyl-N-2,3-dihydroxypropylamino-, N-methyl-N-1,3-dihydroxyisopropylamino-, N-methyl-N-2,3,4,5,6-pentahydroxyhexylamino-, N-2-hydroxyethyl-N-2,3-dihydroxypropylamino-, N-2-hydroxyethyl-N-1,3-dihydroxyisopropylamino-, N,N-bis-(2-hydroxyethyl)amino-, N,N-bis(2,3-dihydroxypropyl)amino-, N,N-bis-(1,3-dihydroxyisopropyl)amino groups.

In compounds of general formula I, the $B_1$, $B_2$, $B_3$ groups preferably are an acetic or an α-propionic group, eventually esterified or substituted by an amido residue which can be in the free form or mono- or bi-substituted by alkyl, hydroxyalkyl, alkoxyalkyl or alkoxyhydroxyalkyl groups.

$R_4$ can preferably be hydrogen or straight or branched lower alkyl, preferably methyl.

Non-limiting examples for $R_4$ are the following: hydrogen, methyl, straight or branched propyl, butyl and pentyl groups, as defined in formula I.

Y can preferably be a hydroxy group or a —O—$R_5$ group, in which $R_5$ has the above defined meanings of formula I.

Non limiting examples of $R_5$ are the following: methyl, ethyl, isopropyl, 2-hydroxyethyl, 2-hydroxypropyl, 1,3-dihydroxyisopropyl, polyoxaalkyl groups.

Y can preferably be also a hydroxyalkylamino group of formula —$NR_6R_7$ in which $R_6$ and $R_7$ have the above mentioned meanings of formula I.

Non-limiting examples of said groups are the following ones:
amino, 2-hydroxyethylamino-, 2-hydroxypropylamino-, 2,3-dihydroxypropylamino-1,3-dihydroxyisopropylamino-, 1,3-dihydroxy-2-methyl-isopropylamino-, 2,3,4-trihydroxy-1-butylamino-, 1,3,4-trihydroxy-2-butylamino-, 1,3-dihydroxy-2-hydroxymethyl-isopropylamino-, N-methyl-N-2-hydroxyethylamino-, N-methyl-N-2,3-dihydroxypropylamino-, N-methyl N-1,3-dihydroxyisopropylamino-, N-methyl-N-2,3,4,5,6-pentahydroxyhexylamino-, N-2-hydroxyethyl-N-2,3-dihydroxypropylamino-, N-2-hydroxyethyl-N-1,3-dihydroxyisopropylamino-, N,N-bis-(2-hydroxyethyl)amino-, N,N-bis-(2,3-dihydroxypropyl)amino-, N,N-bis-(1,3-dihydroxyisopropyl)amino groups.

Metal ions suited to form complex salts with the chelating agents of general formula I are mainly the di- or trivalent ions of the elements having atomic numbers ranging from 20 to 31, 39, 42, 43, 44, 49, or from 57 to 83 and particularly preferred are $Fe^{(2+)}$, $Fe^{(3+)}$, $Cu^{(2+)}$, $Cr^{(3+)}$, $Gd^{(3+)}$, $Eu^{(3+)}$, $Dy^{(3+)}$ or $Mn^{(2+)}$.

Among the metal radioisotopes, particularly preferred are $^{51}Cr$, $^{68}Ga$, $^{111}In$, $^{99m}Tc$, $^{140}La$, $^{168}Yb$.

Preferred inorganic acid anions comprise ions such as chlorides, bromides, iodides or other ions such as sulfate. Preferred organic acid anions comprise ions of acids which are generally pharmaceutically used to salify basic substances, such as acetate, succinate, citrate, fumarate, maleate.

Preferred inorganic base cations comprise alkali metal ions, such as lithium, potassium and sodium, the latter being particularly preferred.

Preferred organic base cations comprise primary, secondary and tertiary amines, such as ethanolamine, diethanolamine, morpholine, glucamine, N,N-dimethyl-glucamine and N-methylglucamine, the latter being preferred.

Preferred amino acid cations comprise, for example, those of lysine, arginine and ornithine.

Non-limiting examples of the macromolecules suited for conjugation with the chelate complexes of the invention are the following: biomolecules, such as hormones (insulin), prostaglandins, steroidal hormones, amino sugars, peptides, proteins (albumin, human serum albumin), lipids, antibodies such as monoclonal antibodies, polysaccharide chains.

The chelated complexes of the invention can also be incorporated into liposomes, used in form of mono- or multi-lamellar vescicles.

The chelating agents of general formula I and the complex salts thereof are preferably prepared by reacting 1,4,7,10-tetraazacyclododecane (II), prepared according to the method of Atkins et al. (JACS 96, 2268 (1974)),

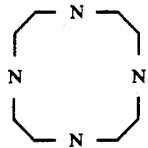
II with the desired α-halo-propionyl derivative III

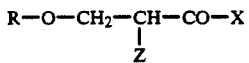
III wherein Z is halogen and R and X have the above defined meanings, to give the addition product IV

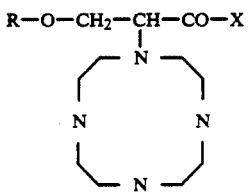
IV or the corresponding polysubstituted products on the nitrogen atoms of II, depending on the excess of III used. Compound IV can also be obtained, for example, by protecting diethylenetriamine V with a suitable protecting group P, wherein P can be, for example, a phthaloyl group or another appropriate protective group known in the literature (T. W. Greene: "Protective groups in organic synthesis"—1980),

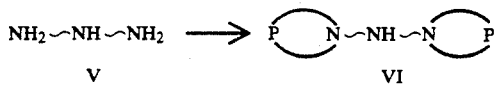

by alkylating the resulting compound VI with the proper halo-derivative III

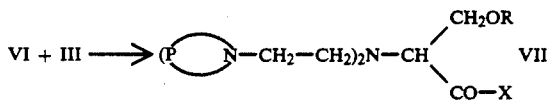
VII and by finally condensing the resulting product VII, after deprotection and subsequent tosylation, with tosyldiethanolamine.

Compound IV or the polysubstituted analogues thereof can in turn be subjected to condensation with the appropriate α-halo-acetic derivative VIII, or with a suitable precursor thereof (such as an ester or a nitrile),

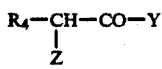
VIII wherein Z is halogen and $R_4$ and Y have the above defined meanings, to give the desired chelating agents of general formula I.

Finally, chelation of the desired metal ion is obtained preferably by reacting the appropriate derivative of formula I with the stoichiometric amount of metal, in form of a salt or an oxide, possibly in the presence of the base or acid amounts necessary for neutralization.

Condensation of II with III is carried out preferably in water or in a dipolar aprotic organic solvent, such as dimethylformamide (DMF) or dimethylacetamide (DMAC) or in a mixture thereof, at a temperature from 30° to 150° C., preferably from 40° to 100° C.

Subsequent condensation of IV with VIII can be effected in an aqueous medium or in an organic solvent, in the presence of an appropriate inorganic or organic base, such as sodium hydroxide, potassium hydroxide, potassium carbonate or tetrabutylammonium hydroxide (TBAOH), at a pH ranging from 8 to 12, preferably from 9 to 11. The temperature can range from 40° to 100° C., preferably from 50° to 70° C.

Finally, preparation of the metal complex salt is preferably carried out in water or in an appropriate water-alcohol mixture, while the temperature can range from 25° to 100° C., preferably from 40° to 80° C.

The choice of the metal ion and, if necessary, of the neutralizing ion is strictly related to the use of the resulting complex.

EXAMPLE 1

2-(1,4,7,10-tetraazacyclododecane-1-yl)-3-benzyloxy-propionic acid, trihydrochloride A) Sodium 2-chloro-3-benzyloxypropionate 85 g of 2-chloro-3-benzyloxypropionic acid (0.396 mol) were suspended in 550 ml of water and neutralized to pH 7 with 10% sodium hydroxide. After stirring for 15 min, the resulting aqueous solution was washed with ethyl ether and evaporated to dryness under vacuum to give the desired compound.

90.6 g sodium 2-chloro-3-benzyloxypropionate (0.383 mol) were obtained.

Yield: 96.7%;

Elemental analysis: % calc.: C 50.75; H 4.26; Cl 14.98. % found: C 50.68; H 4.33; Cl 14.89.

B) 2-(1,4,7,10-tetraazacyclododecane-1-yl)-3-benzyloxy-propionic acid, trihydrochloride A suspension of 17.2 g of 1,4,7,10-tetraazacyclodo-decane (0.1 mol) and of 71 g of sodium 2-chloro-3-benzyloxypropionate (0.3 mol) in 70 ml of water was heated to 50° C. for 24 h. The resulting solution was diluted to 400 ml with water, dropped into 200 ml of 2N HCl, extracted several times with methylene chloride and then was evaporated to dryness under vacuum.

The crude residue was taken up into 400 ml of water and adsorbed on amberlite IR 120, from which it was eluted by means of 5N sodium hydroxide. By concentration of the basic eluate 29 g of a residue were obtained, which were dissolved in 400 ml of absolute ethanol at 60° C.; the solution was acidified with 200 ml of 6N HCl/EtOH and the resulting precipitate was stirred at 60° C. for 1 h. After cooling, the solid was filtered and dried to give the desired compound. 33.5 g of 2-(1,4,7,10-tetraazacyclododecane-1-yl)-3-benzyloxypropionic acid, trihydrochloride (0.0729 mol) were obtained.

Yield: 72.9%; m.p. 221°–224° C.

Titres: (NaOH): 96.9%; (AgNO₃): 99.0%.

Elemental analysis: % calc.: C 47.01; H 7.23; Cl 23.13; N 12.18; % found: C 47.13; H 7.32; Cl 22.92; N 12.09;

TLC: Support: silica gel plate (Merck G60)

Eluent: CHCl$_3$: AcOH: H$_2$O=5:5:1
Developer: Cl$_2$+o-Toluidine
Rf=0.35

$^1$H-NMR, $^{13}$C-NMR and IR spectra agreed with the indicated structure.

EXAMPLE 2

2-[1,4,7,10-tetraaza-7-(1-carboxy-2-benzyloxy-ethyl)-cyclododecane-1-yl]-3-benzyloxypropionic acid A solution of 12 g of 1,4,7,10-tetraazacyclododecane (0.069 mol) and 82.32 g of sodium 2-chloro-3-benzyloxypropionate (0.348 mol), obtained according to the process described in example 1-A, in 120 ml of DMF was placed in a sealed vessel and heated to 50° C. for 30 h.

The salt formed was filtered and the solvent was distilled off under reduced pressure. The residue was taken up into 300 ml of water, the pH was adjusted to 2.5 with 10% hydrochloric acid, then the mixture was extracted with four 50 ml portions of methylene chloride.

The organic phase was evaporated to dryness and the residue was dissolved in 200 ml of 0.01N HCl and washed with ethyl ether.

The pH was adjusted to 6 with 10% sodium hydroxide and the aqueous solution was evaporated to dryness. The crude residue was taken up into 30 ml of water and adsorbed on amberlite IR 120, from which it was eluted with 5N ammonium hydroxide.

By concentration of the basic eluate, a residue of 7 g was obtained, which was crystallized from water.

5.85 g of 2-[1,4,7,10-tetraaza-7(1-carboxy-2-benzyloxyethyl)-cyclododecane-1-yl]-3-benzyloxypropionic acid (0.011 mol) were obtained.

Yield: 16%; m.p.: 170°-175° C.

Elemental analysis: % calc: C 63.61; H 7.63; N 10.60.
% found: C 63.48; H 7.82; N 10.51.

Analogously, the following compounds were obtained:

2-[1,4,7,10-tetraaza-4-(1-carboxy-2-benzyloxy-ethyl)-cyclododecane-1-yl]-3-benzyloxypropionic acid;

2-[1,4,7,10-tetraaza-4,7-di(1-carboxy-2-benzyloxyethyl)cyclododecane-1-yl]-3-benzyloxypropionic acid.

EXAMPLE 3

2-[1,4,7,10-tetraaza-4,7,10-tri(carboxymethyl)-cyclododecane-1-yl]-3-benzyloxypropionic acid (Method A)

To a suspension of 23 g of 2-(1,4,7,10-tetraazacyclododecane-1-yl)-3-benzyloxypropionic acid trihydrochloride (0.05 mol), obtained according to the process described in example 1, and 27.8 g of bromoacetic acid (0.2 mol) in 100 ml of water about 60 ml of 6N sodium hydroxide were added, under stirring, to reach pH=10. The mixture was heated to 50° C. for 17 h and the pH was kept at 10 by further additions of 6N sodium hydroxide.

The solution was cooled and applied to amberlite IR 120, from which the product was eluted with 5N ammonium hydroxide. The basic eluate was evaporated to dryness, the resulting crude compound was dissolved in water and the solution was acidified to pH 3 with 5N HCl.

The precipitate was filtered and crystallized from water to give the desired compound.

15.3 g of 2-[1,4,7,10-tetraaza-4,7,10-tri(carboxymethyl)-cyclododecane-1-yl]-3-benzyloxypropionic acid (0.029 mol) were obtained.

Yield: 58.4%; m.p.: 173° C. with dec.

Titre: (NaOH): 99.6%; (ZnSO$_4$): 99.5%; (HPLC): 99.0%.

Elemental analysis: % calc: C 54.95; H 6.92; N 10.68.
% found: C 54.77; H 6.96; N 10.77.

$^1$H-NMR, $^{13}$C-NMR and IR spectra agreed with the indicated structure.

EXAMPLE 4

2-[1,4,7,10-tetraaza-4,7,10-tri(carboxymethyl)-cyclododecane-1-yl]-3-benzyloxypropionic acid (Method B)

A mixture of 10 g of 2-(1,4,7,10-tetraazacyclododecane-1-yl)-3-benzyloxypropionic acid (0.028 mol), obtained according to the process described in example 1 but without formation of the hydrochloride, and 15.57 g of bromoacetic acid (0.112 mol) in 60 ml of water was treated according to the same process as in example 3, to give the desired compound.

7.93 g of 2-[1,4,7,10-tetraaza-4,7,10-tri(carboxymethyl)-cyclododecane-1-yl]-3-benzyloxypropionic acid (0.015 mol) were obtained.

Yield: 54%; m.p.: 169°-172° C. with dec.

Titre: (NaOH): 99.3%; (ZnSO$_4$): 99.5%.

Elemental analysis: % calc.: C 54.95; H 6.92; N 10.68.
% found: C 54.71; H 7.00; N 10.64.

The other chemico-physical characteristics agreed with the ones of the compound obtained according to method A (example 3).

Analogously, the following compounds were obtained:

2-[1,4,7,10-tetraaza-4,7,10-tri(1-carboxy-ethyl)-cyclododecane-1-yl]-3-benzyloxypropionic acid.

2-[1,4,7,10-tetraaza-4-(1-carboxy-2-benzyloxy-ethyl)-7,10-di(carboxymethyl)-cyclododecane-1-yl]-3-benzyloxypropionic acid.

2-[1,4,7,10-tetraaza-7-(1-carboxy-2-benzyloxy-ethyl)-7,10-di(carboxymethyl)-cyclododecane-1-yl]-3-benzyloxypropionic acid.

2-[1,4,7,10-tetraaza-4,7-di(1-carboxy-2-benzyloxyethyl)10-carboxymethyl-cyclododecane-1-yl]-3-benzyloxypropionic acid.

EXAMPLE 5

D(−)-N-methylglucamine salt of the Gd$^{(3+)}$/2-[1,4,7,10-tetraaza-4,7,10-tri(carboxymethyl)-cyclododecane-1-yl]-3-benzyloxypropionic acid complex.

To a suspension of 100 g of 2-[1,4,7,10-tetraaza-4,7,10-tri(carboxymethyl)-cyclododecane-1-yl]-3-benzyloxypropionic acid (0.19 mol), obtained according to the process described in example 3, in 150 ml of water 36.6 g of D(−)-N-methylglucamine (0.187 mol) were added. 19.47 g of Gd$_2$O$_3$ (0.095 mol) were added to the solution and the resulting suspension was heated to 50° C. for 4 hours. The reaction mixture was filtered and the pH was adjusted to 6.5 by means of a 10% aqueous D(−)-N-methylglucamine solution. The resulting solution was then evaporated and dried to give the desired compound.

159 g of D(−)-N-methylglucamine salt of the Gd$^{(3+)}$/2-[1,4,7,10-tetraaza-4,7,10-tri(carboxymethyl)-cyclododecane-1-yl]-3-benzyloxypropionic acid complex (0.182 mol) were obtained.

Yield: 95.8%; m.p.: 137° C.

Titre: (HPLC): 99.3%.

Elemental analysis: % calc.: C 42.56; H 5.76; Gd 17.99; N 8.01. % found: C 42.42; H 5.96; Gd 17.63; N 7.92.

$[\alpha]_{365}^{20} = -15.36°$; $[\alpha]_{436}^{20} = -11.22°$; $[\alpha]_{546}^{20} = -6.7°$; $[\alpha]_{589}^{20} = -5.7°$; (C=5% H$_2$O).

Analogously, the following compounds were obtained:

Dy$^{(3+)}$/2-[1,4,7,10-tetraaza-4,7,10-tri(carboxymethyl)-cyclododecane-1-yl]-3-benzyloxypropionic acid salt of D(−)-N-methylglucamine, obtained with Dy$_2$O$_3$.

La$^{(3+)}$/2-[1,4,7,10-tetraaza-4,7,10-tri(carboxymethyl)-cyclododecane-1-yl]-3-benzyloxypropionic acid salt of D(−)-N-methylglucamine, obtained with La$_2$O$_3$.

Yb$^{(3+)}$/2-[1,4,7,10-tetraaza-4,7,10-tri(carboxymethyl)-cyclododecane-1-yl]-3-benzyloxypropionic acid salt of D(−)-N-methylglucamine, obtained with Yb$_2$O$_3$.

EXAMPLE 6

D(−)-N-methylglucamine salt of Gd$^{(3+)}$/2-[1,4,7,10-tetraaza-4,7,10-tri(carboxymethyl)-cyclododecane-1-yl]-3-hydroxypropionic acid complex A solution of 92 g of D(−)-N-methylglucamine salt of Gd$^{(3+)}$/2-[1,4,7,10-tetraaza-4,7,10-tri(carboxymethyl)-cyclododecane-1-yl]-3-benzyloxypropionic acid complex (0.105 mol), obtained according to the process described in example 5, in 550 ml of water, to which 153 g of 5% palladium on charcoal had been added, was hydrogenated for 5 h at room temperature.

The catalyst was removed by filtration and the aqueous solution was evaporated under vacuum at 50° C. Upon drying the residue to constant weight, the desired debenzylated compound was obtained.

67 g of D(−)-N-methylglucamine salt of Gd$^{(3+)}$/2-[1,4,7,10-tetraaza-4,7,10-tri(carboxymethyl)-cyclododecane-1-yl]-3-hydroxypropionic acid complex (0.084 mol) were obtained.

Yield: 80%; m.p.: 180° C. (dec.).

Elemental analysis: % calc: C 36.77; H 5.65; Gd 20.06; N 8.93. % found: C 36.47; H 5.47; Gd 20.29; N 8.83.

$[\alpha]_{365}^{20} = -16.7°$; $[\alpha]_{436}^{20} = -11.2°$; $[\alpha]_{546}^{20} = -6.7°$; $[\alpha]_{589}^{20} = -5.8°$ (C=5% H$_2$O).

Analogously, the following compounds were obtained:

2-(1,4,7,10-tetraazacyclododecane-1-yl)-3-hydroxypropionic acid.

2-[1,4,7,10-tetraaza-4-(1-carboxy-2-hydroxy-ethyl)-cyclododecane-1-yl]-3-hydroxypropionic acid.

2-[1,4,7,10-tetraaza-7-(1-carboxy-2-hydroxy-ethyl)-cyclododecane-1-yl]-3-hydroxypropionic acid.

2-[1,4,7,10-tetraaza-4,7-di(1-carboxy-2-hydroxy-ethyl)-cyclododecane-1-yl]-3-hydroxypropionic acid.

2-[1,4,7,10-tetraaza-4-(1-carboxy-2-hydroxy-ethyl)-7,10-di(carboxymethyl)-cyclododecane-1-yl]-3-hydroxypropionic acid.

2-[1,4,7,10-tetraaza-7-(1-carboxy-2-hydroxy-ethyl)-4,10-di(carboxymethyl)-cyclododecane-1-yl]-3-hydroxypropionic acid.

2-[1,4,7,10-tetraaza-4,7-di(1-carboxy-2-hydroxy-ethyl)-10-carboxymethyl-cyclododecane-1-yl]-3-hydroxypropionic acid.

2-[1,4,7,10-tetraaza-4,7,10-tri(carboxymethyl)-cyclododecane-1-yl]-3-hydroxypropionic acid.

EXAMPLE 7

2-(1,4,7,10-tetraazacyclododecane-1-yl)-3-benzyloxy-N-(1,3-dihydroxyisopropyl)-propionamide A) 3-benzyloxy-2-chloropropionylchloride 119 g of thionyl chloride (1 mol) were added dropwise to 107.3 g of 3-benzyloxy-2-chloropropionic acid (0.5 mol) at 30° C. After refluxing the reaction mixture for 2 h, 33 g additional thionyl chloride (0.277 mol) were added and the mixture was refluxed for another 30 min.

Excess thionyl chloride was distilled off under reduced pressure and the desired compound was distilled under vacuum.

95.8 g of 3-benzyloxy-2-chloropropionylchloride (0.41 mol) were obtained.

Yield: 82%; b.p.: 125°-131° C.; 0.05 mbar.

Titre: (reduction with Zn): 99.9%. (Argentometric): 96.0%.

Elemental analysis: % calc: C 51.53%; H 4.32%; Cl 30.42%. % found: C 51.30%; H 4.46%; Cl 29.48%.

$^1$H-NMR, $^{13}$C-NMR and IR spectra agreed with the indicated structure.

B) 2-Chloro-3-benzyloxy-N-(1,3-dihydroxyisopropyl)-propionamide

A solution of 70 g of 3-benzyloxy-2-chloropropionylchloride (0.3 mol) in 150 ml of tetrahydrofuran was added dropwise during about 2 h to a solution of 32.6 g of 2-amino-1,3-dihydroxyisopropane (0.36 mol) in 150 ml of water and 250 ml of tetrahydrofuran. During the addition of the chloride, the pH of the solution was kept constant at 10 by addition of 6N sodium hydroxide.

To the reaction mixture 250 ml of water were added. Upon concentration to 450 ml a white product precipitated, which was filtered and crystallized from water, after treatment with Carbopuron 4N to give the desired compound.

62.2 g of 2-chloro-3-benzyloxy-N-(1,3-dihydroxyisopropyl)-propionamide (0.218 mol) were obtained.

Yield: 72.6%; m.p.: 133°-135° C.

Titre: (Argentometric): 99.8%.

Elemental analysis: % calc: C 54.27; H 6.30; Cl 12.32; N 4.87. % found: C 54.19; H 6.38; Cl 12.24; N 4.84; H$_2$O 0.22.

HPLC: 99%.

$^1$H-NMR, $^{13}$C-NMR and IR spectra agreed with the indicated structure.

C) 2-(1,4,7,10-tetraazacyclododecane-1-yl)-3-benzyloxy-N-(1,3-dihydroxyisopropyl)-propionamide, trihydrochloride 51.6 g of 1,4,7,10-tetraazacyclododecane (0.3 mol) and 258.75 g of 2-chloro-3-benzyloxy-N-(1,3-dihydroxyisopropyl)-propionamide (0.9 mol), obtained according to the process described in example 7B, were reacted at 70° C. in DMF for 24 h.

After evaporation of the solvent under vacuum, the residue was taken up in water and adsorbed on an ion exchange resin IR 120, from which it was eluted by means of 5N ammonium hydroxide.

The ammonia solution was evaporated to dryness and the residue was transformed into the corresponding trihydrochloride, as described in example 1.

63.84 g of 2-(1,4,7,10-tetraazacyclododecane-1-yl)-3-benzyloxy-N-(1,3-dihydroxyisopropyl)-propionamide, trihydrochloride (0.120 mol) were obtained.

Yield: 40.0%; m.p.: 125° C. (dec.).

Elemental analysis: % calc: C 47.33; H 7.56; Cl 19.96; N 13.14. % found: C 47.41; H 7.68; Cl 19.85; N 13.08.

HPLC: 97.6%.

Analogously, the following compounds were obtained:

2-(1,4,7,10-tetraazacyclododecane-1-yl)-3-benzyloxy-propionamide.

2-(1,4,7,10-tetraazacyclododecane-1-yl)-3-benzyloxy-N-(2-hydroxyethyl)-propionamide.

2-(1,4,7,10-tetraazacyclododecane-1-yl)-3-benzyloxy-N-(2,3-dihydroxypropyl)-propionamide.

2-(1,4,7,10-tetraazacyclododecane-1-yl)-3-benzyloxy-N,N-di(2-hydroxyethyl)-propionamide.

EXAMPLE 8

2-[1,4,7,10-tetraaza-4,7,10-tri(carboxymethyl)-cyclododecane-1-yl-]-3-benzyloxy-N-(1,3-dihydroxyisopropyl)-propionamide.

A mixture of 16 g of 2-(1,4,7,10-tetraazacyclododecane-1-yl)-3-benzyloxy-N-(1,3-dihydroxyisopropyl)-propionamide (0.038 mol), obtained according to the process described in example 7, and of 21.13 g of bromoacetic acid (0.152 mol) in 100 ml of water was reacted by the same process as described in example 3, to give the desired compound.

12.4 g of 2-[1,4,7,10-tetraaza-4,7,10-tri(carboxymethyl)-cyclododecane-1-yl]-3-benzyloxy-N-(1,3-dihydroxyisopropyl)-propionamide (0.0207 mol) were obtained.

Yield: 54.4%; m.p.: 137° C. (dec.).

Titre: NaOH 98.8%.

Elemental analysis: % calc.: C 53.98; H 7.72; N 11.66. % found: C 53.91; H 7.85; N 11.59.

Analogously, the following compounds were obtained:

2-[1,4,7,10-tetraaza-4,7,10-tri(carboxymethyl)-cyclododecane-1-yl]-3-benzyloxy-propionamide.

2-[1,4,7,10-tetraaza-4,7,10-tri(carboxymethyl)-cyclododecane-1-yl]-3-benzyloxy-N-(2-hydroxyethyl)-propionamide.

2-[1,4,7,10-tetraaza-4,7,10-tri(carboxymethyl)-cyclododecane-1-yl]-3-benzyloxy-N-(2,3-dihydroxypropyl)-propionamide.

2-[1,4,7,10-tetraaza-4,7,10-tri(carboxymethyl)-cyclododecane-1-yl]-3-benzyloxy-N,N-di(2-hydroxyethyl)-propionamide.

EXAMPLE 9

$Gd^{(3+)}/2$-[1,4,7,10-tetraaza-4,7,10-tri(carboxymethyl)-cyclododecane-1-yl]-3-benzyloxy-N-(1,3-dihydroxyisopropyl)-propionamide To a suspension of 8 g of 2-[1,4,7,10-tetraaza-4,7,10-tri(carboxymethyl)-cyclododecane-1-yl]-3-benzyloxy-N-(1,3-dihydroxyisopropyl)-propionamide (0.013 mol), obtained according to the process described in example 8, in 30 ml of water 1.33 g of $Gd_2O_3$ (0.0065 mol) were added and the mixture was reacted at 50° C. according to the procedure of example 5.

The resulting solution was evaporated to dryness to give the desired product.

9 g of $Gd^{(3+)}/2$-[1,4,7,10-tetraaza-4,7,10-tri(carboxymethyl)-cyclododecane-1-yl]-3-benzyloxy-N-(1,3-dihydroxyisopropyl)-propionamide (0.012 mol) were obtained.

Yield: 92.3%.

Elemental analysis: % calc.: C 42.95; H 5.74; N 9.28. % found: C 42.87; H 5.80; N 9.23.

HPLC: 97.5%.

EXAMPLE 10

$Gd^{(3+)}/2$-[1,4,7,10-tetraaza-4,7,10-tri(carboxymethyl)-cyclododecane-1-yl]-3-hydroxy-N-(1,3-dihydroxyisopropyl)-propionamide 9 g of $Gd^{(3+)}/2$-[1,4,7,10-tetraaza-4,7,10-tri(carboxymethyl)-cyclododecane-1-yl]-3-benzyloxy-N-(1,3-dihydroxyisopropyl)-propionamide (0.012 mol), obtained according to the process described in example 9, were dissolved in 60 ml of water. After addition of 15 g of 5% palladium on charcoal, the solution was hydrogenated according to the procedure of example 6 to give the desired compound.

6.22 g of $Gd^{(3+)}/2$-[1,4,7,10-tetraaza-4,7,10-tri(carboxymethyl)-cyclododecane-1-yl]-3-hydroxy-N-(1,3-dihydroxyisopropyl)-propionamide (0.0096 mol) were obtained.

Yield: 80%.

Elemental analysis: % calc: C 36.13; H 5.61; N 10.53. % found: C 36.06; H 5.64; N 10.48.

Analogously, the following compounds were obtained:

2-(1,4,7,10-tetraazacyclododecane-1-yl)-3-hydroxy-propionamide 2-(1,4,7,10-tetraazacyclododecane-1-yl)-3-hydroxy-N-(2-hydroxyethyl)-propionamide.

2-(1,4,7,10-tetraazacyclododecane-1-yl)-3-hydroxy-N-(2,3-dihydroxypropyl)-propionamide.

2-(1,4,7,10-tetraazacyclododecane-1-yl)-3-hydroxy-N,N-di-(2-hydroxymethyl)-propionamide.

2-[1,4,7,10-tetraaza-4,7,10-tri(carboxymethyl)-cyclododecane-1-yl]-3-hydroxy-propionamide.

2-[1,4,7,10-tetraaza-4,7,10-tri(carboxymethyl)-cyclododecane-1-yl]-3-hydroxy-N-(2-hydroxyethyl)-propionamide.

2-[1,4,7,10-tetraaza-4,7,10-tri(carboxymethyl)-cyclododecane-1-yl]-3-hydroxy-N-(2,3-dihydroxypropyl)-propionamide 2-[1,4,7,10-tetraaza-4,7,10-tri(carboxymethyl)-cyclododecane-1-yl]-3-hydroxy-N,N-di(2-hydroxyethyl)-propionamide.

EXAMPLE 11

Determination of the Relaxivity of the Compounds of the Present Invention

Operative Conditions

| Operative conditions | |
| --- | --- |
| A) Apparatus: | MINISPEC PC 120 (BRUKER) |
| B) Observation frequency: | 20 MHz (proton) |
| C) Temperature: | 39° C., with pre-thermostatization of the NMR test tube for 10 min at the operative temperature |
| D) Concentrations: | in the range from 0 to 5 mM with the following specific measuring points: 0/0.1/0.2/0.5/1.0/2.0/5.0 mM |
| E) Solvent: | 0.154 M NaOH (0.9%), water |
| F) pH: | 7.3, to be checked again potentiometrically before the relaxation measurement. |

Longitudinal relaxivity ($R_1$) measurements were calculated using the "Inversion Recovery" sequence with an 8 point minimum and a 3 parameter fit, according to the program provided for the MINISPEC 120 BRUKER instrument, by which measurements were taken.

Transverse relaxivity ($R_2$) measurements were calculated using the sequence of Carr, Purcell, Meiboom and Gill, according to the program provided for the MINISPEC 120 BRUKER instrument, by means of which measurements were taken, adjusting the apparatus in such a way as to observe the decay of the signal to about ⅛ of the starting value, with a score number higher or equal to 10 and a 2 parameter fit.

In table I, $R_1$ and $R_2$ values calculated for compounds A and B in comparison with Gd/DTPA neutralized with N-methylglucamine, are reported as non-limiting examples.

TABLE I

|  | A $(mM.s)^{-1}$ | B $(mM.s)^{-1}$ | Gd/DTPA* $(mM.s)^{-1}$ |
|---|---|---|---|
| $R_1$ | 4.15 ± 0.01 | 3.72 ± 0.01 | 4.08 ± 0.01 |
| $R_2$ | 5.67 ± 0.02 | 5.06 ± 0.01 | 5.15 ± 0.02 |

A = $Gd^{(3+)}/2$-[1,4,7,10-tetraaza-4,7,10-tri(carboxymethyl)-cyclododecane-1-yl]-3-benzyloxypropionic acid, neutralized with N-methylglucamine.
B = $Gd^{(3+)}/2$-[1,4,7,10-tetraaza-4,7,10-tri(carboxymethyl)-cyclododecane-1-yl]-3-hydroxypropionic acid, neutralized with N-methylglucamine.
*neutralized with N-methylglucamine; $R_1$ and $R_2$ values were determined in aqueous solvent.

EXAMPLE 12

Preparation of liposomes incorporating the $Gd^{(3+)}/2$-[1,4,7,10-tetraaza-4,7,10-tri(carboxymethyl)-cyclododecane-1-yl]-3-benzyloxypropionic acid complex, neutralized with N-methylglucamine An anhydrous lipidic mixture was prepared, having the following composition: egg phosphatidylcholine 75 mol % and cholesterol 25 mol % using the REV method (F. Szoka et al., (1978), Proc. Natl. Acad. Sci. U.S.A. 75,4194).

400 mg of said mixture were dissolved in 35 ml of chloroform to which 10 ml of a 0.05M solution of N-methyl-D-glucamine salt of $Gd^{(3+)}/2$-[1,4,7,10-tetraaza-4,7,10-tri(carboxymethyl)-cyclododecane-1-yl]-3-benzyloxypropionic complex acid were added dropwise under sonication. When the addition was over, sonication was continued for 5 min, then the crude compound was heated to 50° C. and the solvent was evaporated under vacuum. The resulting gelly residue was suspended in a 1% NaCl solution and freed from unincorporated chelate by means of five consecutive centrifugations and resuspension steps (26.000 g/10 min).

EXAMPLE 13

Determination of $LD_{50}$ in the Mouse by Intravenous Administration of the Compounds of the Present Invention In table II are reported, as non-limiting examples, the $LD_{50}$ values for compounds A and B of the present invention, in comparison with $GdCl_3$ and with Gd/DTPA neutralized with N-methylglucamine.

TABLE II

|  | $LD_{50}$ in the mouse* in mmol/kg - intravenous |
|---|---|
| $GdCl_3$ | 0.28 (0.24–0.32) |
| Gd/DTPA** | 4.8 (4.47–5.16) |
| A | 8.8 (7.79–9.94) |
| B | 13.1 (12.2–14.1) |

*male and female mice were used, Strain: Crl:CD1(ICR)BR
**N-methylglucamine salt.
A = $Gd^{(3+)}/2$-[1,4,7,10-tetraaza-4,7,10-tri(carboxymethyl)-cyclododecane-1-yl]-3-benzyloxypropionic acid, neutralized with N-methylglucamine.
B = $Gd^{(3+)}/2$-[1,4,7,10-tetraaza-4,7,10-tri(carboxymethyl)-cyclododecane-1-yl]-3-hydroxypropionic acid, neutralized with N-methylglucamine.

Table II shows that, in this pharmacological test, gadolinium complexes with the macrocyclic chelating agents of the invention have substantially decreased toxicities with respect to both $GdCl_3$ and Gd/DTPA.

EXAMPLE 14

Preparation of a solution of D(−)-N-methylglucamine salt of $Gd^{(3+)}/2$-[1,4,7,10-tetraaza-4,7,10-tri(carboxymethyl)-cyclododecane-1-yl]-3-benzyloxypropionic acid complex 436.8 g (0.500 mol) of the compound obtained according to the procedure described in example 5 were dissolved in 300 ml of pro iniectione (p.i.) water. The solution volume was taken to 500 ml by addition of water p.i., then the solution was filtered, put in vials and sterilized.

EXAMPLE 15

Preparation of a solution of D(−)-N-methylglucamine salt of $Gd^{(3+)}/2$-[1,4,7,10-tetraaza-4,7,10-tri(carboxymethyl)-cyclododecane-1-yl]-3-hydroxypropionic acid complex 398.8 g (0.500 mol) of the compound obtained according to the procedure described in example 6, were dissolved in 300 ml of water p.i. The solution volume was taken to 500 ml by addition of water p.i., then the solution was filtered, put in vials and sterilized.

EXAMPLE 16

Preparation of a solution of D(−)-N-methylglucamine salt of $Gd^{(3+)}/2$-[1,4,7,10-tetraaza-4,7,10-tri(carboxymethyl)-cyclododecane-1-yl]-3-benzyloxypropionic acid complex 218.4 g (0.250 mol) of the salt cited in example 14 were dissolved in 260 ml of water p.i., 0.6 g of ascorbic acid were added and the solution was diluted to 500 ml with water p.i. The solution was sterilized by filtration and put in vials.

EXAMPLE 17

Preparation of a solution of the D(−)-N-methylglucamine salt of $Gd^{(3+)}/2$-[1,4,7,10-tetraaza-4,7,10-tri(carboxymethyl)-cyclododecane-1-yl]-3-benzyloxypropionic acid complex 218.4 g (0.250 mol) of the salt cited in example 14 were dissolved in 200 ml of water p.i., 0.45 g of tromethamine hydrochloride were added and the solution was diluted to 500 ml with water p.i. The solution was filtered, put in vials and sterilized.

EXAMPLE 18

Preparation of a solution of the D(−)-N-methylglucamine salt of Gd$^{(3+)}$/2-[1,4,7,10-tetraaza-4,7,10-tri(carboxymethyl)-cyclododecane-1-yl]-3-hydroxypropionic acid complex 199.4 g (0.250 mol) of the salt cited in example 15 were dissolved in 200 ml of water p.i., 0.6 g of ascorbic acid were added and the solution was diluted to 500 ml with water p.i. The solution was sterilized by filtration and put into vials.

EXAMPLE 19

Preparation of a solution of the D(−)-N-methylglucamine salt of Gd$^{(3+)}$/2-[1,4,7,10-tetraaza-4,7,10-tri(carboxymethyl)-cyclododecane-1-yl]-3-hydroxypropionic acid complex 199.4 g (0.250 mol) of the salt cited in example 15 were dissolved in 200 ml of water p.i., 0.45 g of tromethamine hydrochloride were added and the solution was diluted to 500 ml with water p.i. The solution was filtered, put into vials and sterilized.

We claim:

1. A 1, 4, 7, 10-tetraazacyclododecane compound of formula I

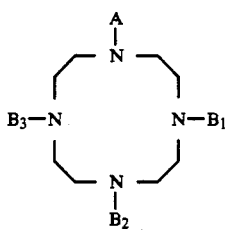

wherein

A is a group of formula

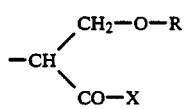

in which

R is H or a $C_1$–$C_5$ straight or branched alkyl group, or a benzyl group which is unsubstituted or mono- or poly-substituted on the aromatic ring by halogen, hydroxy, carboxy, carbamoyl, alkoxycarbonyl, sulphamoyl, lower alkyl, lower hydroxyalkyl, amino, acylamino, acyl, hydroxyacyl groups, or a group of formula H(OCH$_2$CH$_2$)$_{1-4}$—, Me(OCH$_2$CH$_2$)$_{1-4}$—, X is a O—$R_1$ group in which $R_1$ is H or a $C_1$–$C_5$ alkyl, hydroxyalkyl alkoxyalkyl, alkoxyhydroxyalkyl group, or a polyoxaalkyl group having 1 to 15 oxygen atoms and 3 to 45 carbon atoms, or X is a —NR$_2$R$_3$ group in which R$_2$ and R$_3$, are the same or different, and are H, $C_1$–$C_6$ alkyl, hydroxyalkyl, alkoxyalkyl or alkoxyhydroxyalkyl groups having up to 5 hydroxy groups and B$_1$, B$_2$ and B$_3$, are the same or different, and have the same meaning as A or they are H or a group of formula

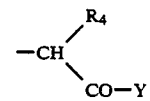

in which

R$_4$ is H or a $C_1$–$C_5$ straight or branched alkyl group,

Y is a O—R$_5$ group in which R$_5$ is H or a $C_1$–$C_5$ alkyl, hydroxyalkyl, alkoxyalkyl, alkoxyhydroxyalkyl group, or a polyoxyalkyl group having 1 to 15 oxygen atoms and 3 to 45 carbon atoms, or Y is a —NR$_6$R$_7$ group in which R$_6$ and R$_7$, are the same or different, and are H or $C_1$–$C_6$ alkyl, hydroxyalkyl, alkoxyalkyl or alkoxyhydroxyalkyl groups having up to 5 hydroxy groups, and a salt of said compound of formula I with an organic base which is a member selected from the group consisting of primary, secondary, tertiary amines or with a basic aminoacid or with an inorganic base having a cation which is sodium, potassium or lithium, and a chelate of said compound of formula I or of a salt thereof with a di- or trivalent ion of a metal element having atomic number ranging from 20 to 31,39,42 to 44,49, 57 to 83, wherein said chelate is neutral or acidic or salified with an organic base which is a member selected from the group consisting of primary, secondary, tertiary amines or with a basic aminoacid or with an inorganic base having a cation which is sodium, potassium or lithium.

2. 1,4,7,10-Tetraazacyclododecane derivatives of general formula II

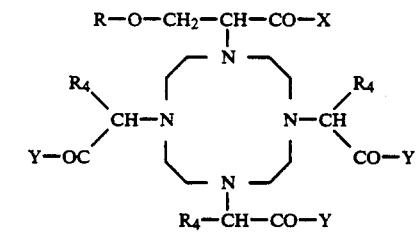

wherein

R,R$_4$,X and Y have the meanings defined in claim 1, and the chelates thereof with appropriate bi- or trivalent ions of metal elements having atomic numbers from 20 to 31, 39, 42, 43, 44, 49 or from 57 to 83.

3. 1,4,7,10-Tetraazacyclododecane derivatives of general formula III

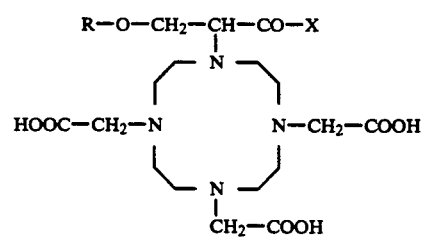

wherein R and X have the meanings defined in claim 1, and the chelates thereof with appropriate bi- or trivalent ions of metal elements having atomic numbers from 20 to 31, 39, 42, 43, 44, 49 or from 57 to 83.

4. Serine derivatives of general formula IV

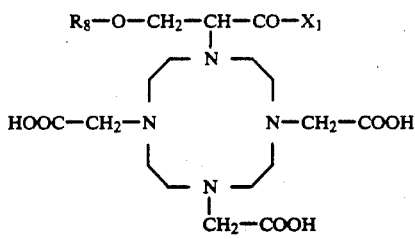

wherein $R_8$ is H or benzyl, $X_1$ is OH, $-NH_2$, $-NHCH_2CH_2OH$, $-NHCH(CH_2OH)_2$, $-NHCH_2CH(OH)CH_2OH$, $-N(CH_2CH_2OH)_2$, $-NH-CH_2-CH(OH)-CH_2OCH_3$ or $-NH-CH_2-CH(OH)-CH(OH)-CH_2OH$, and the chelates thereof with appropriate bi- or trivalent ions of metal elements having atomic numbers from 20 to 31, 38, 42, 43, 44, 49, or from 57 to 83.

5. A chelate of a compound as claimed in claim 1, in which the chelate metal ion if $Fe^{(2+)}$, $Fe^{(3+)}$, $Cu^{(2+)}$, $Gd^{(3+)}$, $Eu^{(3+)}$, $Dy^{(3+)}$ or $Mn^{(2+)}$.

6. Chelates as claimed in claim 2 with the ions of the following radioisotopes: $^{51}Cr$, $^{68}Ga$, $^{111}In$, $^{99m}Tc$, $^{140}La$, $^{168}Yb$.

7. A compound as claimed in claim 1, selected from the group consisting of:
2-(1,4,7,10-tetraazacyclododecane-1-yl)-3-benzyloxypropionic acid,
2-(1,4,7,10-tetraazacyclododecane-1-yl)-3-hydroxypropionic acid,
2-[1,4,7,10-tetraaza-4-(1-carboxy-2-benzyloxy-ethyl)-cyclododecane-1-yl]-3-benzyloxypropionic acid,
2-[1,4,7,10-tetraaza-4-(1-carboxy-2-hydroxy-ethyl)-cyclododecane-1-yl]-3-hydroxypropionic acid,
2-[1,4,7,10-tetraaza-7-(1-carboxy-2-benzyloxy-ethyl)-cyclododecane-1-yl]-3-benzyloxypropionic acid,
2-[1,4,7,10-tetraaza-7-(1-carboxy-2-hydroxy-ethyl)-cyclododecane-1-yl]-3-hydroxypropionic acid,
2-[1,4,7,10-tetraaza-4,7-di(1-carboxy-2-benzyloxy-ethyl)-cyclododecane-1-yl]-3-benzyloxypropionic acid,
2-[1,4,7,10-tetraaza-4,7-di(1-carboxy-2-hydroxy-ethyl)-cyclododecane-1-yl]-3-hydroxypropionic acid,
2-[1,4,7,10-tetraaza-4-(1-carboxy-2-benzyloxy-ethyl)-7,10-di(carboxymethyl)-cyclododecane-1-yl]-3-benzyloxypropionic acid,
2-[1,4,7,10-tetraaza-4-(1-carboxy-2-hydroxy-ethyl)-7,10-di(carboxymethyl)-cyclododecane-1-yl]-3-hydroxypropionic acid,
2-[1,4,7,10-tetraaza-7-(1-carboxy-2-benzyloxy-ethyl)-4,10-di(carboxymethyl)-cyclododecane-1-yl]-3-benzyloxypropionic acid,
2-[1,4,7,10-tetraaza-7-(1-carboxy-2-hydroxy-ethyl)-4,10-di(carboxymethyl)-cyclododecane-1-yl]-3-hydroxypropionic acid,
2-[1,4,7,10-tetraaza-4,7-di(1-carboxy-2-benzyloxy-ethyl)-10-carboxymethyl-cyclododecane-1-yl]-3-benzyloxypropionic acid,
2-[1,4,7,10-tetraaza-4,7-di(1-carboxy-2-hydroxy-ethyl)-10-carboxymethyl-cyclododecane-1-yl]-3-hydroxypropionic acid,
2-[1,4,7,10-tetraaza-4,7,10-tri(carboxymethyl)-cyclododecane-1-yl]-3-benzyloxypropionic acid,
2-[1,4,7,10-tetraaza-4,7,10-tri(carboxymethyl)-cyclododecane-1-yl]-3-hydroxypropionic acid,
2-(1,4,7,10-tetraazacyclododecane-1-yl)-3-benzyloxypropionamide,
2-(1,4,7,10-tetraazacyclododecane-1-yl)-3-hydroxy-propionamide,
2-(1,4,7,10-tetraazacyclododecane-1-yl)-3-benzyloxy-N-(2-hydroxyethyl)-propionamide,
2-(1,4,7,10-tetraazacyclododecane-1-yl)-3-hydroxy-N-(2-hydroxyethyl)-propionamide,
2-(1,4,7,10-tetraazacyclododecane-1-yl)-3-benzyloxy-N-(1,3-dihydroxyisopropyl)-propionamide,
2-(1,4,7,10-tetraazacyclododecane-1-yl)-3-hydroxy-N-(1,3-dihydroxyisopropyl)-propionamide,
2-(1,4,7,10-tetraazacyclododecane-1-yl)-3-benzyloxy-N-(2,3-dihydroxypropyl)-propionamide,
2-(1,4,7,10-tetraazacyclododecane-1-yl)-3-hydroxy-N-(2,3-dihydroxypropyl)-propionamide,
2-(1,4,7,10-tetraazacyclododecane-1-yl)-3-benzyloxy-N,N-di(2-hydroxyethyl)-propionamide,
2-(1,4,7,10-tetraazacyclododecane-1-yl)-3-hydroxy-N,N-di-(2-hydroxyethyl)-propionamide,
2-[1,4,7,10-tetraaza-4,7,10-tri(carboxymethyl)-cyclododecane-1-yl]-3-benzyloxy-propionamide,
2-[1,4,7,10-tetraaza-4,7,10-tri(carboxymethyl)-cyclododecane-1-yl]-3-hydroxy-propionamide,
2-[1,4,7,10-tetraaza-4,7,10-tri(carboxymethyl)-cyclododecane-1-yl]-3-benzyloxy-N-(2-hydroxyethyl)-propionamide,
2-[1,4,7,10-tetraaza-4,7,10-tri(carboxymethyl)-cyclododecane-1-yl]-3-hydroxy-N-(2-hydroxyethyl)-propionamide,
2-[1,4,7,10-tetraaza-4,7,10-tri(carboxymethyl)-cyclododecane-1-yl]-3-benzyloxy-N-(1,3-dihydroxyisopropyl)-propionamide,
2-[1,4,7,10-tetraaza-4,7,10-tri(carboxymethyl)-cyclododecane-1-yl]-3-hydroxy-N-(1,3-dihydroxyisopropyl)-propionamide,
2-[1,4,7,10-tetraaza-4,7,10-tri(carboxymethyl)-cyclododecane-1-yl]-3-benzyloxy-N-(2,3-dihydroxypropyl)-propionamide,
2-[1,4,7,10-tetraza-4,7,10-tri(carboxymethyl)-cyclododecane-1-yl]-3-hydroxy-N-(2,3-dihydroxypropyl)-propionamide,
2-[1,4,7,10-tetraaza-4,7,10-tri(carboxymethyl)-cyclododecane-1-yl]-3-benzyloxy-N,N-di(2-hydroxyethyl)-propionamide,
2-[1,4,7,10-tetraaza-4,7,10-tri(carboxymethyl)-cyclododecane-1-yl]-3-hydroxy-N,N-di(2-hydroxyethyl)-propionamide,
the respective chelate complexes with $Fe^{(3+)}$, $Cu^{(2+)}$, $Mn^{(2+)}$, $Gd^{(3+)}$, $Dy^{(3+)}$, $In^{(3+)}$, $La^{(3+)}$, $Yb^{(3+)}$ and the corresponding salts with D(−)-N-methylglucamine.

8. A method for the preparation of a metal chelate of a 1,4,7,10-tetraazacyclododecane compound of formula I

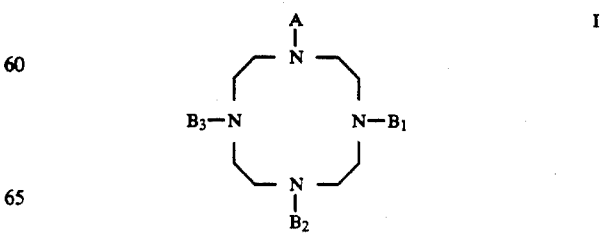

wherein

A is a group of formula

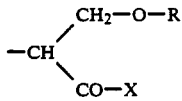

in which

R is H or a $C_1$–$C_5$ straight or branched alkyl group, or a benzyl group which is unsubstituted or mono- or poly-substituted on the aromatic ring by halogen, hydroxy, carboxy, carbamoyl, alkoxycarbonyl, sulphamoyl, lower alkyl, lower hydroxyalkyl, amino, acylamino, acyl, hydroxyacyl groups, or a group of formula $H(OCH_2CH_2)_{1-4}$—, $Me(OCH_2CH_2)_{1-4}$— or $Et$-$(OCH_2CH_2)_{1-4}$—, X is a O—$R_1$ group in which $R_1$ is H or a $C_1$–$C_5$ alkyl, hydroxyalkyl, alkoxyalkyl, alkoxyhydroxyalkyl group, or a polyoxaalkyl group having 1 to 15 oxygen atoms and 3 to 45 carbon atoms, or X is a —$NR_2R_3$ group in which $R_2$ and $R_3$, are the same or different, and are $C_1$–$C_6$ alkyl, hydroxyalkyl, alkoxyalkyl or alkoxyhydroxyalkyl groups having up to 5 hydroxy groups and $B_1$, $B_2$ and $B_3$, are the same or different, and have the same meaning as A or they are H or a group of formula

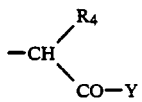

in which $R_4$ is H or a $C_1$–$C_5$ straight or branched alkyl group, Y is a O—$R_5$ group in which $R_5$ is H or a $C_1$–$C_5$ alkyl, hydroxyalkyl, alkoxyalkyl, alkoxyhydroxyalkyl group, or a polyoxaalkyl group having 1 to 15 oxygen atoms and 3 to 45 carbon atoms, or Y is a —$NR_6R_7$ group in which $R_6$ and $R_7$ are the same or different, and are H or $C_1$–$C_6$ alkyl, hydroxyalkyl, alkoxyalkyl or alkoxyhydroxyalkyl groups having up to 5 hydroxy groups, which consists in reacting a salt or an oxide of a metal selected from the metals having atomic numbers from 20 to 31, 39,42,43,44,49 or from 57 to 83 with said compound of formula I or a salt thereof in the presence of an acid or a base in an amount necessary for neutralization.

9. A compound according to claim 1 which is the D(−)-N-methylglucamine salt of the chelate complex of Gd(3+) with 2-[1,4,7,10-tetraaza-4,7-di(1-carboxy-2-benzyloxy-ethyl)-10-carboxymethyl-cyclododecane-1-yl]-3-benzyloxypropionic acid.

10. A compound according to claim 1 which is the Gd (3+)complex with 2-[1,4,7,10-tetraaza-4,7,10-tri(-carboxymethyl)-cyclododecane-1-yl]-3-benzyloxy-[N-methyl-N(D-1-deoxyglucitol)]-propionamide.

11. A compound according to claim 1 which is the Gd(3+)complex with 2-[1,4,7,10-tetraaza-4,7,10-tri(-carboxymethyl)-cyclododecane-1-yl]-3-(L)-benzyloxy-N-methyl-N(D-1-deoxyglucitol)]-propionamide.

12. A compound according to claim 1 which is Gd(3+)complex with 2-[1,4,7,10-tetraaza-4,7,10-tri(-carboxymethyl)-cyclododecane-1-yl]3-hydroxy-[N-methyl-N-(D)-1-deoxy-glucitol)]-propionamide.

13. A compound according to claim 1 which is the Gd(3+)complex with 2-[1,4,7,10-tetraaza-4,7,10-tri(-carboxymethyl)-cyclododecane-1-yl]3-(L)-hydroxy-[N-methyl-N-(D-1-deoxyglucitol)]-propionamide.

14. The compound according to claim 1 wherein said organic base is ethanolamine, diethanolamine, morpholine, glucamine, N,N-dimethylglucamine or N-methylglucamine.

15. The compound according to claim 1 wherein said basic aminoacid is lysine, arginine or ornithine.

16. The compound according to claim 1 wherein said inorganic base is sodium hydroxide, potassium hydroxide or lithium hydroxide.

17. The method according to claim 8 wherein said acid necessary for the neutralization is an inorganic or organic acid, said inorganic acid having an anion which is a member selected from the group consisting of chloride, bromide, iodide or sulfate, said organic acid being acetic, succinic, citric, fumaric or maleic.

18. The method according to claim 8 wherein said base necessary for neutralization is an inorganic or organic base, said inorganic base having a cation which is sodium, potassium or lithium, said organic base being a primary, secondary or tertiary amine or a basic aminoacid.

* * * * *

UNITED STATES PATENT AND TRADEMARK OFFICE
CERTIFICATE OF CORRECTION

PATENT NO. : 5,132,409
DATED : July 21, 1992
INVENTOR(S) : Ernst Felder, Carlo Musu, Luciano Fumagalli, Fulvio Uggeri It is certified that error appears in the above-indentified patent and that said Letters Patent is hereby corrected as shown below:

On the title page: Item [30] FOREIGN PRIORITY DATA should read --23217 A/87--.

Signed and Sealed this

Tenth Day of January, 1995

Attest:

BRUCE LEHMAN

Attesting Officer

Commissioner of Patents and Trademarks